United States Patent
Grant et al.

(10) Patent No.: US 9,029,162 B2
(45) Date of Patent: May 12, 2015

(54) METHODS AND SYSTEMS FOR DETERMINING THE PRESENCE OR AMOUNT OF TESTOSTERONE IN A SAMPLE

(75) Inventors: Russell Philip Grant, Chapel Hill, NC (US); Matthew Crawford, Mebane, NC (US); Donald Walt Chandler, Agoura Hills, CA (US); William Curtin, Northridge, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 13/367,997

(22) Filed: Feb. 7, 2012

(65) Prior Publication Data

US 2012/0238027 A1 Sep. 20, 2012

Related U.S. Application Data

(60) Provisional application No. 61/440,282, filed on Feb. 7, 2011.

(51) Int. Cl.

| | |
|---|---|
| *G01N 33/74* | (2006.01) |
| *G01N 27/62* | (2006.01) |
| *G01N 30/72* | (2006.01) |
| G01N 33/48 | (2006.01) |
| G01N 30/04 | (2006.01) |
| G01N 30/88 | (2006.01) |

(52) U.S. Cl.
CPC ............ *G01N 30/7233* (2013.01); *G01N 33/48* (2013.01); *G01N 33/743* (2013.01); *G01N 30/04* (2013.01); *G01N 2030/8831* (2013.01)

(58) Field of Classification Search
CPC ....... G01N 33/48; G01N 33/68; G01N 33/74; G01N 33/743; G01N 2030/8831; G01N 30/72; G01N 30/7233; G01N 30/02; G01N 30/022; G01N 30/04
USPC ............... 436/56, 63, 71, 127, 128, 131, 161, 436/173, 174, 175, 177, 178; 422/68.1, 69, 422/70; 250/281, 282; 210/656, 198.2
See application file for complete search history.

(56) References Cited

U.S. PATENT DOCUMENTS

| | | | | |
|---|---|---|---|---|
| 5,618,807 | A * | 4/1997 | Barrie et al. | 514/176 |
| 8,153,962 | B2 * | 4/2012 | Ghoshal et al. | 250/282 |
| 2004/0235193 | A1 * | 11/2004 | Soldin | 436/518 |
| 2006/0040256 | A1 | 2/2006 | Caulfield et al. | |
| 2008/0128606 | A1 | 6/2008 | Grant et al. | |
| 2008/0261312 | A1 | 10/2008 | Yang | |
| 2009/0215111 | A1 | 8/2009 | Veenstra et al. | |
| 2010/0022487 | A1 * | 1/2010 | Hyde et al. | 514/170 |
| 2010/0227412 | A1 * | 9/2010 | Cerda | 436/131 |

FOREIGN PATENT DOCUMENTS

| | | |
|---|---|---|
| CN | 101551362 | 10/2009 |
| CN | 101802606 | 8/2010 |

OTHER PUBLICATIONS

Zomer et al. Abstract from Steroids, vol. 44, No. 4, Oct. 1984, pp. 283-292.*
Draisci et al. Journal of High Resolution Chromatography, vol. 20, Aug. 1997, pp. 421-426.*
Cleeve, Matthew. American Laboratory, Feb. 1, 2008, pp. 1-5.*
International Search Report for PCT/US12/24187, dated May 18, 2012.
Chinese Application No. 201280013364.2, Office Action mailed Jan. 19, 2015, With English Translation, 20 pages.
Pan et al., Automatic Supported Liquid Extraction (SLE) Coupled with HILIC-MS/MS: An Application to Method Development and Validation of Erlotinib in Human Plasma, Pharmaceutics, 2:105-118 (2010).
Singh, R.J., Validation of a high throughput method for serum/plasma testosterone using liquid chromatography tandem mass spectrometry (LC-MS/MS), Steroids, 73(13): 1339-44 (2008); Abstract only.
Wu et al., Supported Liquid Extraction in Combination with LC-MS/MS for High-Throughput Quantitative Analysis of Hydrocortisone in Mouse Serum, Biomed. Chromatography, 24: 632-638 (2010).

* cited by examiner

*Primary Examiner* — Maureen Wallenhorst
(74) *Attorney, Agent, or Firm* — Kilpatrick Townsend & Stockton LLP

(57) ABSTRACT

Disclosed are methods and systems for the analysis of testosterone in a sample using supported liquid extraction and liquid chromatography-mass spectrometry.

23 Claims, No Drawings

METHODS AND SYSTEMS FOR DETERMINING THE PRESENCE OR AMOUNT OF TESTOSTERONE IN A SAMPLE

CROSS-REFERENCE TO RELATED APPLICATIONS

The present application claims the benefit of priority of U.S. Provisional Patent Application No. 61/440,282, filed Feb. 7, 2011, which is incorporated by reference as though fully set forth herein.

FIELD OF INVENTION

The present invention provides methods and systems for determining the presence or amount of a biomarker in a sample. In particular, the invention provides methods and systems for analyzing testosterone in a sample using liquid chromatography and mass spectrometry.

BACKGROUND

Biomarkers, such as hormones, vitamins, and/or metabolites, can be used for the clinical diagnosis of multiple disorders and as endogenous biomarkers in endocrinology. Steroid hormones, such as testosterone, are an important class of hormones. Testosterone develops and maintains male secondary sex characteristics, and promotes growth and development of sperm.

The adrenals and gonads synthesize testosterone. Levels can be elevated in patients with congenital adrenal hyperplasia due to enzyme block, which decreases cortisol production and increases precursor levels directed toward the androgenic pathway. Testosterone may also be elevated in women with hirsutism. The ovary may be a significant source of this hormone in these patients. Testosterone is normally much higher in adult men than it is in women and children due to production in the testis. Levels in men may be decreased in hypogonadal states.

Requirements for the clinical diagnostic testing of endogenous biomarkers in endocrinology may include highly sensitive and specific assays, the ability to analyze small sample volumes (e.g., pediatric sample volumes can be limited to less than about 200 μL), and the ability to screen for multiple analytes to accurately diagnose a disease state, e.g., an endocrine disorder. Historically, radioimmunoassay (RIA) and enzyme-linked immunoassay (ELISA) methods have been used in such clinical diagnostic testing. Immunoassay methods (IA), such as RIA and EIA, however, may suffer from low throughput, antibody cross-reactivity, which can require extra preparation for specificity, and poor scalability. Also, the analysis of endogenous biomarkers by RIA may require multiple serial dilutions for the analysis of each individual marker, which can lead to the need to make multiple adjustments to normalize sample volumes and/or the need for multiple separate tests. Also, immunoassay testing is not particularly conducive to the analysis of multiple biomarkers in each sample. The analysis for multiple analytes in a single assay can allow for using samples of reduced size which results in assays of increased sensitivity and efficiency per sample.

Thus, there is a need to develop analytical techniques that can be used for the measurement of endogenous biomarkers, and for methods that provide more sensitivity and higher throughput than RIA. Until recently, however, only GC-MS or LC-MS/MS with derivatization has been successful for small sample volumes. Thus, there is a need in the art for LC-MS/MS techniques for the analysis of endogenous biomarkers for clinical diagnosis in endocrinology capable of providing detection limits at acceptable levels, without the need for the cumbersome derivatization processes.

SUMMARY OF THE INVENTION

In at least one aspect, the invention provides methods for determining the presence or amount of testosterone in a sample, the methods comprising: (a) providing a sample containing testosterone; (b) partially purifying the sample using supported liquid extraction, thereby providing a partially purified sample comprising testosterone; (c) chromatographically separating testosterone from the other components in the partially purified sample using liquid chromatography; and (d) analyzing the chromatographically separated testosterone by mass spectrometry to determine the presence or amount of testosterone in the sample. Further embodiments of these methods are described in detail below.

In another aspect, the invention provides methods for determining the amount of testosterone in a biological sample, the methods comprising: (a) providing a sample, the sample comprising a biological sample that contains testosterone; (b) partially purifying the sample using supported liquid extraction, thereby providing a partially purified sample comprising testosterone; (c) chromatographically separating testosterone from the other components in the partially purified sample using reverse phase liquid chromatography; and (d) analyzing the chromatographically separated testosterone by mass spectrometry to determine the amount of testosterone in the biological sample. Further embodiments of these methods are described in detail below.

In another aspect, the invention provides methods of generating a report useful for diagnosing a disease or condition associated with abnormal testosterone levels, the methods comprising: (a) providing a sample, the sample comprising a biological sample that contains testosterone; (b) partially purifying the sample using supported liquid extraction to provide a partially purified sample comprising testosterone; (c) chromatographically separating testosterone from the other components in the partially purified sample using liquid chromatography; (d) analyzing the chromatographically separated testosterone by mass spectrometry to determine the amount of testosterone in the biological sample; and (e) generating a report that recites the concentration of testosterone in the biological sample. Further embodiments of these methods are described in detail below.

In another aspect, the invention provides systems for determining the presence or amount of testosterone in a sample, the systems comprising: (a) a station for partially purifying a sample using supported liquid extraction, the sample comprising testosterone; (b) a station for chromatographically separating testosterone from the other components in the partially purified sample using liquid chromatography; and (c) a station for analyzing the chromatographically separated testosterone by mass spectrometry to determine the presence or amount of testosterone in the sample. Further embodiments of these methods are described in detail below.

Further aspects of the invention are described in detail below.

BRIEF DESCRIPTION OF THE DRAWINGS

Not applicable.

DETAILED DESCRIPTION

The following description recites various aspects and embodiments of the present invention. No particular embodiment is intended to define the scope of the invention. Rather, the embodiments merely provide non-limiting examples various methods and systems that are at least included within the scope of the invention. The description is to be read from the perspective of one of ordinary skill in the art; therefore, information well known to the skilled artisan is not necessarily included.

Various abbreviations may be used in the application. In most, if not all, instances, the meanings of such abbreviations are known to those of skill in the art. These abbreviations include the following abbreviations, whose meanings are provided.

APCI=atmospheric pressure chemical ionization
CBP=competitive binding protein
HTLC=high turbulence (throughput) liquid chromatography
HPLC=high performance liquid chromatography
LLE=liquid-liquid extraction
LOQ=limits of quantification
LLOQ=lower limit of quantification
IA=immunoassay
ELISA=enzyme linked immunoassay
RIA=radioimmunoassay
SST=system suitability test
ULOQ=upper limit of quantification
2D-LC-MS/MS=two-dimensional liquid chromatography hyphenated to tandem mass spectrometry
(LC)-LC-MS/MS=two-dimensional liquid chromatography tandem hyphenated to mass spectrometry
(LC)-MS/MS=liquid chromatography hyphenated to tandem mass spectrometry
SLE=supported liquid extraction

DEFINITIONS

The following terms, unless otherwise indicated, shall be understood to have the following meanings:

As used herein, the terms "a," "an," and "the" can refer to one or more unless specifically noted otherwise.

As used herein, the term "biomarker" is any biomolecule that may provide biological information about the physiological state of an organism. In certain embodiments, the presence or absence of the biomarker may be informative. In other embodiments, the level of the biomarker may be informative. A biomarker may be a hormone, such as an testosterone, or a metabolite of a hormone.

Throughout this application, the term "about" is used to indicate that a value includes the inherent variation of error for the device, the method being employed to determine the value, or the variation that exists among the study subjects.

As used herein, the terms "subject," "individual," and "patient" are used interchangeably. The use of these terms does not imply any kind of relationship to a medical professional, such as a physician.

As used herein, the phrase "liquid chromatography" or "LC" is used to refer to a process for the separation of one or more molecules or analytes in a sample from other analytes in the sample. LC involves the slowing of one or more analytes of a fluid solution as the fluid uniformly moves through a column of a finely divided substance. The slowing results from the distribution of the components of the mixture between one or more stationery phases and the mobile phase. LC includes, for example, reverse phase liquid chromatography (RPLC) and high pressure liquid chromatography (HPLC).

As used herein, the term "separate" or "purify" or the like are not used necessarily to refer to the removal of all materials other than the analyte of interest from a sample matrix. Instead, in some embodiments, the terms are used to refer to a procedure that enriches the amount of one or more analytes of interest relative to one or more other components present in the sample matrix. In some embodiments, a "separation" or "purification" may be used to remove or decrease the amount of one or more components from a sample that could interfere with the detection of the analyte, for example, by mass spectrometry.

As used herein, the term "mass spectrometry" or "MS" analysis refers to a technique for the identification and/or quantitation of molecules in a sample. MS includes ionizing the molecules in a sample, forming charged molecules; separating the charged molecules according to their mass-to-charge ratio; and detecting the charged molecules. MS allows for both the qualitative and quantitative detection of molecules in a sample. The molecules may be ionized and detected by any suitable means known to one of skill in the art. The phrase "tandem mass spectrometry" or "MS/MS" is used herein to refer to a technique for the identification and/or quantitation of molecules in a sample, wherein multiple rounds of mass spectrometry occur, either simultaneously using more than one mass analyzer or sequentially using a single mass analyzer. As used herein, a "mass spectrometer" is an apparatus that includes a means for ionizing molecules and detecting charged molecules.

As used herein, "electrospray ionization" or "ESI" refers to a technique used in mass spectrometry to ionize molecules in a sample while avoiding fragmentation of the molecules. The sample is dispersed by the electrospray into a fine aerosol. The sample will typically be mixed with a solvent, usually a volatile organic compound (e.g., methanol or acetonitrile) mixed with water. The aerosol is then transferred to the mass spectrometer through a capillary, which can be heated to aid further solvent evaporation from the charged droplets.

As used herein, a "quadrupole analyzer" is a type of mass analyzer used in MS. It consists of four circular rods (two pairs) that are set highly parallel to each other. The quadrupole analyzer is the component of the instrument that organizes the charged particles of the sample based on their mass-to-charge ratio. One of skill in the art would understand that use of a quadrupole analyzer can lead to increased specificity of results. One pair of rods is set at a positive electrical potential and the other set of rods is at a negative potential. To be detected, an ion must pass through the center of a trajectory path bordered and parallel to the aligned rods. When the quadrupoles are operated at a given amplitude of direct current and radio frequency voltages, only ions of a given mass-to-charge ratio will resonate and have a stable trajectory to pass through the quadrupole and be detected. As used herein, "positive ion mode" refers to a mode wherein positively charged ions are detected by the mass analyzer, and "negative ion mode" refers to a mode wherein negatively charged ions are detected by the mass analyzer. For "selected ion monitoring" or "SIM," the amplitude of the direct current and the radio frequency voltages are set to observe only a specific mass.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 µm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns," which typically are used to separate or extract retained materials from non-retained materials to obtained a "purified" sample for further purification or analysis. In some embodiments, the extraction column is a functionalized silica or polymer-silica hybrid or polymeric particle or monolithic silica stationary phase, such as a Poroshell SBC-18 column.

The term "heart-cutting" refers to the selection of a region of interest in a chromatogram and subjecting the analytes eluting within that region of interest to a second separation, e.g., a separation in a second dimension.

As used herein, the term "hemolysed" refers to the rupturing of the red blood cell membrane, which results in the release of hemoglobin and other cellular contents into the plasma or serum and the term "lipemic" refers to an excess of fats or lipids in blood.

Methods for Determining the Presence or Amount of Testosterone

In at least one aspect, the invention provides methods for determining the presence or amount of testosterone in a sample, the methods comprising: (a) providing a sample containing testosterone; (b) partially purifying the sample using supported liquid extraction, thereby providing a partially purified sample comprising testosterone; (c) chromatographically separating testosterone from the other components in the partially purified sample using liquid chromatography; and (d) analyzing the chromatographically separated testosterone by mass spectrometry to determine the presence or amount of testosterone in the sample.

These methods comprise providing a sample containing testosterone. In this context, the term "providing" is to be construed broadly. The term is not intended to refer exclusively to a subject who provided a biological sample. For example, a technician in an off-site clinical laboratory can be said to "provide" the sample, for example, as the sample is prepared for purification by extraction and/or chromatography.

The sample is not limited to any particular sample type. The sample contains testosterone, but, in general, also includes other components. In some embodiments, the sample is a sample that has been processed and prepared for purification by extraction and/or chromatography. Such processing may be useful for optimizing the effectiveness of subsequent purification steps. Such processing methods are well known to those of skill in the art.

The invention is not limited to any particular means of sample handling. In some embodiments, it may be useful to separate the sample into two or more fractions prior to purification by extraction and/or chromatography. In some such embodiments, two or more of such fractions may be prepared differently, for example, to help improve the sensitivity or selectivity of the separation for a particular column chemistry. In some embodiments, the method includes preparing a single sample for repeat injections across multiple liquid chromatography systems.

The invention is not limited to any particular sample size. In some embodiments, the sample comprises a biological sample. In such embodiments, the sample may also include other components, such as solvents, buffers, anticlotting agents and the like. In embodiments where the sample comprises a biological sample, the biological sample can be one or more of whole blood, plasma, serum, urine, cerebrospinal fluid, tissue homogenate, saliva, amniotic fluid, bile, mucus, peritoneal fluid, or lymphatic fluid.

Further, the testosterone in the sample is not limited to any particular form of testosterone. For example, testosterone includes carbon, oxygen, and hydrogen atoms. Each of these atoms has naturally occurring isotopes. Thus, some amount of the testosterone in the sample may bear one or more of such naturally occurring isotopes. The term also includes cationic and anionic forms (e.g., salted forms), if present. In contrast, this specification refers specifically to a testosterone ion (or ionized testosterone) in the discussion of analysis of testosterone by mass spectrometry. In such instances, described below, only ionized testosterone is referred to.

The method further comprises partially purifying the sample using supported liquid extraction (SLE). As noted above, the sample may contain, in addition to testosterone and one or more solvents, various other components. Thus, the partial purification of the sample provides a partially purified sample comprising testosterone. In some embodiments, the concentrations of one or more of the various other components have been removed, meaning that their concentrations have been reduced relative to the concentration of testosterone in the partially purified sample. Thus, the term "removing" or "removal" does not necessarily imply the complete removal of a component. Some amount of the removed component can still be present in the partially purified sample, although its concentration relative to that of testosterone will be lower than in the pre-extraction sample. In some embodiments, the relative concentration of the removed component to that of testosterone in the partially purified sample is no more than 90%, or no ore than 75%, or no more than 50%, or no more than 33%, or no more than 25%, or no more than 10%, or no more than 5%, or no more than 1%, of its relative concentration to testosterone in the pre-extraction sample.

The invention is not limited to any particular type of removed component. In some embodiments, one or more of the removed components is a compound that can interfere with the analysis of testosterone by mass spectrometry, for example, because the compound may have a similar mass to testosterone or because, upon fragmentation, it generates one or more fragment ions that have the same mass as one or more fragments generated by fragmenting testosterone. Such compounds include, but are not limited to cortisone, cortisol, 21-desoxycortisol, corticosterone, 11-desoxycortisol, triamcinolone acetonide, tetrahydrocortisol, tetrahydro-cortisone, DHEA, 17a-hydroxyprogesterone, epitesterone, dihydroandrosterone, 5a-androstan-3a-ol-17-one, 5b-pregnane-3a-17a-20a-triol, etiocolan-3a-diol, and pregnanediol.

The invention is not limited to any particular manner of performing SLE. In some embodiments, the sample is absorbed onto an inert solid-phase material. Various such materials can be used. In some embodiments, the sample is absorbed onto diatomaceous earth. The sample is them contacted with a organic water-immiscible solvent system. Such solvents systems are well known in the art. The organic water-immiscible solvent system includes, but is not limited to ethyl acetate, hexane, toluene, octanol, chloroform, dichloromethane, diethyl ether, cyclohexane, pentane, N-heptanes, benzene, n-butyl chloride, butanol, methylene chloride, and mixtures of any two or more of the foregoing. In some embodiments, the organic water-immiscible solvent system can also include some amount of one or more polar solvents. In such embodiments, the amount of polar solvent must be sufficiently low to ensure that the solvent system remains generally water-immiscible. Suitable polar solvents for use in such embodiments include, but are not limited to methanol, acetone, acetonitrile, isopropanol, diethyl ether, or methyl-t- butyl ether. In some embodiments, the organic water-immiscible solvent used in the SLE comprises a mixture of dichloromethane and hexane.

The SLE can be carried out using any suitable apparatus designed therefor. Suitable apparatuses include, but are not limited to plates and columns. In some embodiments, the SLE employs one or more plates. In some such embodiments, the SLE employs a plate having multiple wells, such as a 96-well plate. Such plates are commercially available. Furthermore, the SLE can be carried out manually or in an automated manner. Further, the partially purifying step can, in some embodiments, be accompanied by applying mechanical action to the SLE apparatus to facilitate extraction. Such mechanical action can include agitation, vibration, and the like.

In some embodiments of the invention, the partially purified sample can undergo one or more processing steps before chromatographic separation. For example, in some embodiments, the partially purified sample is evaporated. Then, the resulting residue is reconstituted in a solvent system. Any suitable solvent system can be used for reconstituting the testosterone-containing residue. In some embodiments, the solvent system is a solvent system that is compatible with chromatographic separation. In some embodiments, the solvent system for reconstitution includes, but is not limited to, water, methanol, or mixtures thereof.

The methods comprise chromatographically separating testosterone using liquid chromatography. The invention is not limited to any particular manner of performing liquid chromatography. In general, the chromatographic separation step includes using at least one liquid chromatography (LC) column. In some embodiments, multiple LC columns are used, such as two or more, or three or more, or four or more LC columns. In some such embodiments two, three, four, five, six, eight, or ten LC columns are used. In some such embodiments, two or more of these LC columns are arranged parallel to each other, and are connected inline to the same mass spectrometer.

The invention is not limited to any particular types of columns. Any column suitable for the separation of testosterone can be used. In some embodiments, one or more analytical columns are used. In some such embodiments, one or more reverse phase columns are used. In some embodiments, the method employs two or more reverse phase columns in parallel, which are connected inline to the same mass spectrometer.

Further, the invention is not limited to any particular mobile phase. Any suitable mobile phase can be used, as long as the mobile phase is suitable for use with a particular LC column and for chromatographically separating testosterone in the LC column. In some embodiments, the mobile phase is a polar solvent system. The polar solvent system can include one or more polar solvents, including but not limited to water, methanol, acetonitrile, or a mixture of two or more of the foregoing. In some such embodiments, the mobile phase employs a gradient, such that the relative ratios of two or more solvents are varied over time.

As noted above, two or more LC columns (e.g., reverse phase columns) can be used in parallel and connected inline to the same mass spectrometer, e.g., to improve throughput. In some such embodiments, a testosterone-containing sample (i.e., the partially purified sample, e.g., following evaporation and reconstitution) is introduced to the two or more LC columns at different times. In some embodiments, the introduction of the test sample to the two or more LC columns is staggered, meaning that there is a pre-determined time interval separating the introduction of sample to two or more LC columns. Appropriate time intervals can be selected based on various factors, including the elution time, column chemistries, and the potential need to avoid interfering with the analysis of the testosterone eluted from one or more of the other LC columns.

In some embodiments of the invention, another LC column can be placed in series with another column. For example, in some embodiments, suitable guard columns can be employed. Those of skill in the art are able to select appropriate guard columns for use in the present methods. In some embodiments, a guard column is placed in parallel with another LC column, and both the guard column and the LC column are reverse phase columns. Such series of two or more columns can also be arranged in parallel, such that there are two or more series of columns operating in parallel, where each series contains two or more columns.

The methods comprise analyzing the chromatographically separated testosterone by mass spectrometry to determine the presence or amount of testosterone. In some embodiments, two or more of the LC columns feed into the same mass spectrometer. In some further embodiments, three or more of the LC columns feed into the same mass spectrometer. In some embodiments, the mass spectrometer is part of a combined LC-MS system.

The invention is not limited to any particular type of mass spectrometer. Any suitable mass spectrometer can be used. In some embodiments, the method employs a tandem mass spectrometer. In some such embodiments, analyzing testosterone can include, ionizing testosterone, analyzing the ionized testosterone, fragmenting the testosterone ion into two or more fragment ions, and analyzing the fragment ions. The invention is not limited to a mass spectrometer using any particular ionization methods. Any suitable ionization can be used. Suitable ionization methods include, but are not limited to photoionization, electrospray ionization, atmospheric pressure chemical ionization, and electron capture ionization. And in embodiments that employ fragmenting, any suitable fragmentation technique can be used. Suitable techniques include, but are not limited to collision induced dissociation, electron capture dissociation, electron transfer dissociation, infrared multiphoton dissociation, radiative dissociation, electron-detachment dissociation, and surface-induced dissociation.

In some embodiments, the tandem mass spectrometer is a MDS-Sciex API5000 triple quadrupole mass spectrometer. In some embodiments, the tandem mass spectrometer has an atmospheric pressure ionization source, and the analyzing step comprises an ionization method selected from the group consisting of photoionization, electrospray ionization (ESI), atmospheric pressure chemical ionization (APCI), electron capture ionization, electron ionization, fast atom bombardment/liquid secondary ionization (FAB/LSI), matrix assisted laser desorption ionization (MALDI), field ionization, field desorption, thermospray/plasmaspray ionization, and particle beam ionization. The ionization method may be in positive ion mode or negative ion mode. The analyzing step may also include multiple reaction monitoring or selected ion monitoring (SIM), and the two or more biomolecules are analyzed simultaneously or sequentially. In some embodiments, the analyzing step uses a quadrupole analyzer. In some embodiments, the mass spectrometer is a triple quadrupole mass spectrometer.

The methods, in some embodiments, include using an internal standard. In such embodiments, the internal standard can be introduced at any suitable point prior to the chromatographic separation step. Any suitable internal standard can be used. In some embodiments, the internal standard is stable isotopically-labeled testosterone. In some such embodiments, the internal standard is labeled by carbon-13 and/or deuterium. In some embodiments, the internal standard is 2,3,4-$^{13}$C-labeled testosterone.

In some embodiments, the amount of testosterone need not be determined. In some embodiments, the method can be used to determine the presence or absence of testosterone in a sample. In other embodiments, the method is used to determine the amount of testosterone in a sample. For example, in some embodiments and/or aspects, the invention provides methods for determining the amount of testosterone in a biological sample, the methods comprising: (a) providing a sample, the sample comprising a biological sample that contains testosterone; (b) partially purifying the sample using supported liquid extraction, thereby providing a partially purified sample comprising testosterone; (c) chromatographically separating testosterone from the other components in the partially purified sample using reverse phase liquid chromatography; and (d) analyzing the chromatographically separated testosterone by mass spectrometry to determine the amount of testosterone in the biological sample.

In some embodiments, the method is not limited by any lower-limit and/or upper-limit of detection. In some embodiments, the methods can be used to measure testosterone in a sample (e.g., a sample comprising a biological sample) at concentrations that range from 2.5 ng/dL to 5000 ng/dL, or from 5 ng/dL to 5000 ng/dL, or from 10 ng/dL to 5000 ng/dL, or from 2.5 ng/dL to 2000 ng/dL.

Methods of Generating Reports

In at least one aspect, the invention provides methods for generating a report for diagnosing a disease or condition associated with an abnormal level of testosterone in a subject, the methods comprising: (a) providing a sample, the sample comprising a biological sample that contains testosterone; (b) partially purifying the sample using supported liquid extraction to provide a partially purified sample comprising testosterone; (c) chromatographically separating testosterone from the other components in the partially purified sample using liquid chromatography; (d) analyzing the chromatographically separated testosterone by mass spectrometry to determine the amount of testosterone in the biological sample; and (e) generating a report that recites the concentration of testosterone in the biological sample.

The features and embodiments of all steps except step (e) are described immediately above. As noted above, the method can employ more than one column, e.g., two or more columns in parallel connected inline to the same mass spectrometer.

The method further includes generating a report that recites the amount of at least one testosterone in the sample. In some embodiments, this information can be used to determine the concentration of testosterone in a biological sample. From such information, one could assess whether a subject has an abnormally high or low amount of testosterone.

Such information can be useful for diagnosing one or more diseases or disorders that may be associated with aberrant levels of testosterone in a subject. Such diseases or conditions are well known in the art. Such diseases or conditions include but are not limited to congenital adrenal hyperplasia, hirsutism, and various hypergonadal states.

Systems for Analyzing Biomolecules

In another aspect, the invention provides systems for determining the presence or amount of testosterone in a sample, the systems comprising: (a) a station for partially purifying a sample using supported liquid extraction, the sample comprising testosterone; (b) a station for chromatographically separating testosterone from the other components in the partially purified sample using liquid chromatography; and (c) a station for analyzing the chromatographically separated testosterone by mass spectrometry to determine the presence or amount of testosterone in the sample.

Such systems can include various embodiments and sub-embodiments analogous to those described above for methods of analyzing testosterone.

These systems include various stations. As used herein, the term "station" is broadly defined and includes any suitable apparatus or collections of apparatuses suitable for carrying out the recited method. The stations need not be integrally connected or situated with respect to each other in any particular way. The invention includes any suitable arrangements of the stations with respect to each other. For example, the stations need not even be in the same room. But in some embodiments, the stations are connected to each other in an integral unit.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Analysis for Testosterone $^{13}$C-testosterone is added to serum aliquots to evaluate and correct for recovery of the testosterone from each sample. Testosterone is diluted 1:1 with a buffer and then added to an SLE+ plate. Testosterone is extracted from serum and plasma samples with a mixture of hexane and dichloromethane. Samples are evaporated and reconstituted with a methanol/water solution. Samples are then injected onto an LC-MS/MS system. An MDS-Sciex API5000 triple quadrupole mass spectrometer, operating in positive ion atmospheric pressure chemical ionization mode is used for detection. Quantification of analyte and internal standard is performed in selected reaction monitoring mode (SRM). The back-calculated amount of the individual analyte in each sample is determined from calibration curves generated by spiking known amounts of purified analyte into charcoal stripped serum from 2.5 to 5000 ng/dL.

Specimens

A recommended sample is 0.3-0.8 mL serum or plasma. Serum collected using standard sampling tubes or tubes containing separating gel. Serum/Plasma should be removed from the cells within one hour of collection and transferred to a plastic transport tube. Serum and plasma should be stored in a freezer at −20° C. until used.

Equipment & Materials

The following supplies and instruments were used.

Manual pipettes w/tips; Class A volumetric pipettes and flasks; Assorted glass reagent bottles; PARAFILM (Fisher Healthcare); Easy Pierce Heat Sealing Foil (Fisher Healthcare); Multi-Tube Vortex (Fisher Scientific); Turbovap Plate Evaporator (Biotage, LLC); Thermo Manual Heat Sealer ALPS25 or equivalent (Thermo Scientific); 96-well polypropylene deep well plates (SPEware Corp.); 96-well SLE+400 plates (Biotage, LLC); Agilent Zorbax XDB C-18 2.1×50, 5 um (Krackeler Scientific); and VacMaster-96 Sample Processing Manifold System (Biotage, LLC).

96-well plate 5804R Centrifuge or equiv. (Eppendorf); API 5000 Tandem Mass Spectrometer and Turbo V™ Ion Source with APCI (Sciex, Toronto, Canada); Aria Transcend TX4 System consisting of 8 1200SL Series Binary Pumps and 4 1200 Series Vacuum Degasser (Thermo-Fisher, MA, USA); HTS Twin PAL System Autosampler (CTC Analytics AG, Switzerland); Analyst version 1.4 or greater (Applied Biosystems, CA, USA); Aria OS version 1.6 or greater (Thermo-Fisher, MA, USA).

Reagents

The following reagents were used:

Testosterone (USP); [$^{13}$C3]-Testosterone (Isosciences); Methylene Chloride (Fisher Healthcare); Hexane (Fisher Healthcare); Methanol (Fisher Healthcare); Charcoal Stripped Human Serum (Golden West); Pooled Serum (In-house collection); Ethanol (Sigma-Aldrich); Formic Acid (Sigma-Aldrich); Acetonitrile (Fisher Healthcare).

The following solvents were used as the mobile phases for liquid chromatography:

Extraction Solvent (50:50 Hexane:Methylene Chloride): Measure 500 mL hexane in a graduated cylinder and transfer to a 1 L bottle. Measure 500 mL methylene chloride separately in a graduated cylinder and add to the 1 L bottle containing the hexane. Mix well.

Eluting Pump A Mobile Phase (0.1% Formic Acid in Millipore $H_2O$): Measure 999 mL of Type I Millipore water and pour into a 1 L reagent bottle. In a fume hood slowly add 1 mL formic acid to the Millipore $H_2O$. Mix well.

Eluting Pump B Mobile Phase (0.1% Formic Acid in Acetonitrile): Measure 999 mL of acetonitrile and pour into a 1 L reagent bottle. In a fume hood slowly add 1 mL formic acid to the acetonitrile. Mix well.

Internal Standard Stock (1 mg/mL): Weigh approximately 10 mg [$^{13}$C3]-testosterone into a glass scintillation vial on an analytical balance. After adjusting for purity, add the appropriate amount of methanol to bring solution to a final concentration of 1 mg/mL. Mix well to dissolve. Store at −20° C.; stable for at least one year in glass scintillation vials.

Internal Standard Stock Solution (10000 ng/mL): Add 1 mL of [$^{13}$C3]-testosterone internal standard stock (1 mg/mL) to a 100 mL Class A volumetric flask and Q.S. to volume with MeOH. Mix well. Final concentration is 10000 ng/dL. Store frozen (−20° C.); stable for at least one year.

Working Internal Standard Solution (120 ng/dL): Add 0.12 mL of [$^{13}$C3]-testosterone internal standard stock (10000 ng/mL) to a 1000 mL Class A volumetric flask and Q.S. to volume with 50:50 MeOH: Millipore $H_2O$. Mix well. Final concentration is 120 ng/dL. Alternate volumes may be prepared at the same concentration and composition. Store refrigerated (2-8° C.).

Reconstitution Solution (1:1 Methanol:Water): Add 500 mL of HPLC grade methanol to a 1 liter glass reagent bottle. Add 500 mL of Type I water to the same bottle. Mix well and store at room temperature.

Testosterone System Suitability Test Solution (SST): Inject 35 µL of the working internal standard solution (120 ng/dL) to establish system suitability prior to submitting the batch for analysis. The system suitability injection employed 35 µL injection of 120 ng/dL [$^{13}$C3]-testosterone in 50:50 methanol:water; acceptance criteria: all analytes 0.05-0.30 minutes; peak intensity≥12000 cps for the 292/100 transition.

Needle Wash Solution 1 (0.1% Formic Acid in Millipore $H_2O$): Measure 999 mL of Type I Millipore water and pour into a 1 L reagent bottle. In a fume hood slowly add 1 mL formic acid to the Millipore $H_2O$. Mix well.

Needle Wash Solution 2 (Methanol): Transfer 1000 mL methanol to a glass bottle. Store at room temperature.

Calibration

Calibrators are prepared and testing for accuracy at Esoterix Endocrinology, Calabasas, Calif., USA. Bulk material are shipped to CET on dry ice where it will then be subaliquoted and stored. Sub-aliquots are stored at −20° C. for 5.58 years.

A full set of Calibrators are to be included at the beginning of each analytical batch. An extra Blank+IS, LLOQ and ULOQ are to be added as the last three samples of each batch Quality Control Quality control samples are prepared and tested to establish ranges at Esoterix Endocrinology, Calabasas Calif., USA. Bulk material are shipped to CET on dry ice where it are then subaliquoted and stored. Sub-aliquots are stored at −20° C. for 5.58 years.

Manual Procedure

Prepare batch: Thaw and mix standards, samples and controls. Label a set of 12×75 mm glass test tubes for each sample, control and standard.

Pipette samples: Pipette 200 µL of blanks, standards, controls, and samples into the appropriately labeled tube. Pipette 200 µL working internal standard solution to each tube except double blanks Double blanks receive 400 µL Millipore water. Mix rack of tubes on multi-vortexer for 1 minute.

Transfer to 96-well plate: Place a 96-well deep well plate into the bottom half the VacMaster-96 sample processing manifold. Replace the top section of the manifold over the deep well plate and position a SLE+400 plate on top of the manifold so that the wells are in alignment with the deep well collection plate underneath. Transfer all samples to the SLE+ 400 96-well plate using a multichannel pipette or equivalent.

SLE Extraction: Place the manifold (containing the plates) under a fume hood and connect the tubing to a vacuum source. Apply slight vacuum (5 mmHg) to draw sample into SLE+ plate, and then wait for 5-10 minutes. Using a 12-channel pipette (or equivalent) aspirate and dispense the 50:50 Hexane: Methylene Chloride 3 times. Then add 900 µL of the extraction solvent across each row. Apply slight vacuum for 15-20 seconds and then wait 10 minutes to allow the extraction solvent to pass through to the deep well plate. After 10 minutes, apply high vacuum pressure for 30 seconds to draw off the remaining extraction solvent into the 96-well collection plate.

Evaporation/Reconstitution: Place the 96-well collection plate into the Turbovap plate evaporator. Evaporate plates at approx 40 psi and 40° C. for approximately 20 minutes or until dry. Reconstitute each well with 100 µL of Reconstitution Solution (1:1 MeOH:Millipore $H_2O$). Seal plate and mix briefly for 1 minute. Centrifuge for 5 minutes.

LC: Fill all LC system reagents. Prime the LC pumps to remove any bubbles from mobile phase lines or to remove mobile phase from a previous assay/batch (if new mobile phase was made). When all system(s) and autosampler(s) are ready, click "Start". Inject 35 µL of sample.

Automated Procedure

Prepare batch: Thaw and mix standards, samples, and controls. Initialize the TECAN Freedom EVO instrument as advised in standard operating procedure NOQS-SOP-13, section 10-Procedures.

Pipette samples: Place a computer/lab generated barcode label on the corresponding blanks, standards, and QC tubes. In an empty source rack place bar coded tubes in the following order: Double Blank, Blank+IS, Standard 1-8, and Double Blank. Add patient samples beginning in position 12 of source rack 1 continuing through source rack 12. Two (2)

sets of quality control samples are to be randomly placed throughout the assay. Note: Only 12×75 mm sized tubes may be used as source tubes for patient samples. Transfer tubes other than this size must be poured off into the correct tube size and bar-coded accordingly. Load source racks onto the TECAN Freedom EVO deck.

Transfer to 96-well plate: Place 96-deep well plates on the deck. Place eight 16×100 mm glass test tubes in position 1-8 of an empty source rack and fill each with working internal standard solution. Place one 16×100 mm test glass test tube in position 16 of the same source rack as the internal standard tubes and fill with Type I water. Place source rack containing internal standard and Type I water in the appropriate position on the deck. Ensure 1000 µL DiTi Tips are loaded on the TECAN Freedom EVO deck.

In the application software, select Testosterone script. Click Run to begin script. The TECAN will first scan all tubes and create the scan.csv file. When prompted check the file created and corrected any barcode related issues. Then click okay to continue the script. The TECAN will now add 200 µL of blanks, standard, patient sample, and quality control sample to the 96-deep well plates. When prompted visually confirm all samples have been pipetted correctly. Sample may be added manually with an appropriate pipette in the event sample was not added. A notation should be made on the batch coversheet. If any sample volume does not appear consistent with the other sample a note should be made on the batch coversheet. Click okay to continue.

The TECAN will add 200 µL type I water to vial positions A1 of the 1st 96-deep well plate and 2004 of working internal standard solution are added to the rest of the vial positions. While internal standard is being added to the 96-deep well plates, initialize the BIOMEK FX liquid handler. Remove the 96-deep well plates from the TECAN Freedom EVO automated pipetting instrument and place it on the BIOMEK FX automated liquid handler.

SLE Extraction: Place an SLE+ plate on top of a 96-deep well plate and position it on the BIOMEK FX deck. Ensure AP200 pipette tips are loading in the appropriate position. In the application software select either 1 Plate SLE Transfer or 2 Plate SLE Transfer script depending on the number of samples in the assay. Click on the green start button in the top tool bar. The BIOMEK FX will first mix the sample and internal standard before transferring the contents of the 96-deep well plate to the SLE+ plate in a two step process. In the event sample is not transferred by the BIOMEK, it is permissible to do so manually while taking caution to transfer sample to the appropriate well.

Place a 96-well deep well plate into the bottom half the VacMaster-96 sample processing manifold. Replace the top section of the manifold over the deep well plate and position a SLE+400 plate on top of the manifold so that the wells are in alignment with the deep well collection plate underneath. Place the manifold (containing the plates) under a fume hood and connect the tubing to a vacuum source. Apply slight vacuum (5 mm Hg) to draw sample into SLE+ plate, then wait for 5-10 minutes.

Using a 12-channel pipette (or equivalent) aspirate and dispense the 50:50 Hexane:Methylene Chloride 3 times. Then add 900 µL of the extraction solvent across each row. Apply slight vacuum for 15-20 seconds and then wait 10 minutes to allow the extraction solvent to pass through to the deep well plate. After 10 minutes, apply high vacuum pressure for 30 seconds to draw off the remaining extraction solvent into the deep well collection plate.

Evaporation/Reconstitution: Place the 96-well collection plate into the Turbovap plate evaporator. Evaporate plates at approx 40 psi and 40° C. for approximately 20 minutes or until dry. Reconstitute each well with 100 µL of Reconstitution Solution (1:1 MeOH:Millipore $H_2O$). Seal plate and mix briefly for 1 minute. Centrifuge for 5 minutes.

LC: Fill all LC system reagents. Prime the LC pumps to remove any bubbles from mobile phase lines or to remove mobile phase from a previous assay/batch (if new mobile phase was made). When all system(s) and autosampler(s) are ready, click "Start". Inject 35 µL of sample.

Reporting Results

Units for this assay in serum and plasma are in nanograms per deciliter (ng/dL).

Results are reported as one decimal place for serum and plasma samples.

The lower limit of quantification for this assay is 2.5 ng/dL. Values below 2.5 ng/dL are to be reported out as <2.5 ng/dL. The upper limit of detection is 5000 ng/dL. Values above 5000 ng/dL are to be diluted up to 50-fold with Type I water. With the inclusion of dilution the upper limit of quantification would be 250000 ng/dL. If sufficient specimen is not available to repeat on a dilution, >10000 is to be entered with a "QNSR" abbreviation attached. This abbreviation notifies the account that there is insufficient specimen to verify results.

Provisional Reference Intervals

|  | Male Range (ng/dL) | Female Range (ng/dL) |
|---|---|---|
| Premature Inafnts |  |  |
| 26-28 weeks, day 4 | 59-125 | 5-16 |
| 31-35 weeks, day 4 | 37-198 | 5-22 |
| Full Term Infants |  |  |
| Newborns | 75-400 | 20-64 |

Male 1-7 Months: Levels decrease rapidly the first week to 20-50 ng/dL, then increase to 60-400 ng/dL (mean=190) between 20-60 days. Levels then decline to prepubertal range of <2.5-10 by seven months.

Female 1-7 Months: Levels decrease during the first month to <10 ng/dL and remain there until puberty.

| Prepubertal Children | |
|---|---|
| 1-10 Years | <2.5-10 |

| Puberty | | | | | | | |
|---|---|---|---|---|---|---|---|
| Tanner Stage | Age (years) | Range (ng/dL) | Mean (ng/dL) | Tanner Stage | Age (years) | Range (ng/dL) | Mean (ng/dL) |
| | | Male | | | | Female | |
| 1 | <9.8 | <2.5-10 | 4.9 | 1 | <9.2 | <2.5-10 | 4.9 |
| 2 | 9.8-14.5 | 18-150 | 42 | 2 | 9.2-13.7 | 7-28 | 18 |

-continued

| Puberty | | | | | | | |
|---|---|---|---|---|---|---|---|
| Tanner Stage | Age (years) | Range (ng/dL) | Mean (ng/dL) | Tanner Stage | Age (years) | Range (ng/dL) | Mean (ng/dL) |
| | Male | | | | Female | | |
| 3 | 10.7-15.4 | 100-320 | 190 | 3 | 10.0-14.4 | 15-35 | 25 |
| 4 | 11.8-16.2 | 200-620 | 372 | 4 | 10.7-15.6 | 13-32 | 22 |
| 5 | 12.8-17.3 | 350-970 | 546 | 5 | 11.8-18.6 | 20-38 | 28 |

| Adults 20-50 Years | Range (ng/dL) |
|---|---|
| Male: | 350-1030 |
| Female: | |
| Premenopausal | 10-55 |
| Postmenopausal | 7-40 |

Example 2

Test Results for Centers for Disease Control (CDC) Data

The analysis method described in Example 1 was used to determine the testosterone levels in samples obtained from the CDC having standardized levels of testosterone (referred to as "CDC challenge sets"). Two different CDC challenge sets were tested. For each of the ten samples in the two sets, four replicates were done over the course of two days. Thus, the reported mean, standard deviation, and CV are for an n of 4.

Challenge Set 1

| Sample | Mean (ng/dL) | St. Dev. (ng/dL) | CV (%) | % Diff from CDC Ref Value |
|---|---|---|---|---|
| 1 | 316.328 | 4.999 | 1.58 | 3.0 |
| 2 | 482.422 | 9.267 | 1.92 | 3.7 |
| 3 | 453.931 | 4.650 | 1.02 | 3.4 |
| 4 | 646.568 | 13.141 | 2.03 | 2.1 |
| 5 | 433.878 | 7.760 | 1.79 | 2.9 |
| 6 | 20.043 | 0.703 | 3.51 | -4.6 |
| 7 | 465.605 | 7.426 | 1.59 | 3.9 |
| 8 | 18.940 | 1.207 | 6.37 | -0.8 |
| 9 | 8.221 | 0.531 | 6.46 | -3.2 |
| 10 | 460.537 | 5.867 | 1.27 | 2.1 |

Challenge Set 2

| Sample | Mean (ng/dL) | St. Dev. (ng/dL) | CV (%) | % Diff from CDC Ref Value |
|---|---|---|---|---|
| 1 | 5.584 | 0.176 | 3.15 | -2.9 |
| 2 | 291.020 | 1.788 | 0.61 | 5.2 |
| 3 | 758.221 | 13.382 | 1.79 | 3.9 |
| 4 | 22.118 | 0.141 | 0.64 | -0.4 |
| 5 | 3.406 | 0.099 | 2.91 | -6.9 |
| 6 | 12.261 | 0.388 | 3.17 | -0.3 |
| 7 | 165.671 | 0.940 | 0.57 | 3.5 |
| 8 | 640.736 | 5.973 | 0.93 | 4.4 |
| 9 | 24.684 | 0.371 | 1.50 | 0.8 |
| 10 | 7.472 | 0.081 | 1.09 | -3.1 |

We claim:

1. A method for determining the presence or amount of testosterone in a biological sample, the method comprising:
(a) providing a biological sample containing testosterone;
(b) partially purifying the biological sample using supported liquid extraction, thereby providing a partially purified sample comprising testosterone, wherein the supported liquid extraction includes using diatomaceous earth and an organic water-immiscible solvent system, and wherein the organic water-immiscible solvent system comprises a solvent selected from the group consisting of hexane, octanol, chloroform, dichloromethane, diethyl ether, cyclohexane, pentane, N-heptanes, benzene, n-butyl chloride, butanol, methylene chloride, and mixtures thereof;
(c) chromatographically separating testosterone from the other components in the partially purified sample using liquid chromatography, wherein the liquid chromatography comprises using at least one guard column; and
(d) analyzing the chromatographically separated testosterone by mass spectrometry to determine the presence or amount of testosterone in the biological sample;
wherein the step of partially purifying the biological sample using supported liquid extraction comprises eluting with the organic water-immiscible solvent system under slight vacuum and under gravity.

2. The method of claim 1, wherein the partially purifying step (b) includes removing components that interfere with the analysis of testosterone by mass spectrometry.

3. The method of claim 2, wherein the components that interfere with the analysis of testosterone by mass spectrometry include one or more of: cortisone, cortisol, 21-desoxycortisol, corticosterone, 11-desoxycortisol, triamcinolone acetonide, tetrahydrocortisol, tetrahydro-cortisone, DHEA, 17a-hydroxyprogesterone, epitesterone, dihydroandrosterone, 5a-androstan-3a-ol-17-one, 5b-pregnane-3a-17a-20a-triol, etiocolan-3a-diol, or pregnanediol.

4. The method of claim 1, wherein the organic water-immiscible solvent system further comprises an amount of a polar solvent, where the polar solvent is methanol, acetone, acetonitrile, isopropanol, diethyl ether, or methyl-tert-butyl ether.

5. The method of claim 1, wherein the partially purifying step (b) is carried out in an automated fashion.

6. The method of claim 1, wherein the partially purifying step (b) is carried out manually.

7. The method of claim 1, wherein using liquid chromatography includes using analytical liquid chromatography.

8. The method of claim 7, wherein using analytical liquid chromatography includes using a reverse phase column.

9. The method of claim 7, wherein using liquid chromatography includes using at least one column.

10. The method of claim 7, wherein using liquid chromatography includes using two or more liquid chromatography columns in parallel, where the two or more liquid chromatography columns are connected inline to a single mass spectrometer.

11. The method of claim 10, wherein using two or more liquid chromatography columns in parallel includes introducing the partially purified sample to the two or more liquid chromatography columns at staggered times.

12. The method of claim 1, wherein the analyzing step (d) includes ionizing testosterone using an ionization technique selected from the group consisting of: electrospray ionization, atmospheric pressure chemical ionization, and atmospheric pressure photoionization.

13. The method of claim 1, wherein the analyzing step (d) includes detecting testosterone using a quadrupole mass spectrometer.

14. The method of claim 13, wherein the quadrupole mass spectrometer is a triple quadrupole mass spectrometer.

15. The method of claim 14, wherein the analyzing step (d) includes: detecting intact testosterone ion in a first quadrupole; fragmenting intact testosterone ion in a second quadrupole to yield one or more testosterone fragment ions; and detecting the one or more testosterone fragment ions in a third quadrupole.

16. The method of claim 1, wherein the analyzing step (d) includes determining the amount of testosterone in the biological sample.

17. The method of claim 1, wherein the biological sample comprises an internal standard.

18. The method of claim 17, wherein the internal standard is a stable isotopically-labeled testosterone.

19. The method of claim 18, where the internal standard is a $^{13}$C-labeled testosterone.

20. The method of claim 19, where the internal standard is 2,3,4-$^{13}$C-labeled testosterone.

21. A method for determining the amount of testosterone in a biological sample, the method comprising:
 (a) providing a biological sample comprising testosterone;
 (b) partially purifying the biological sample using supported liquid extraction, thereby providing a partially purified sample comprising testosterone, wherein the supported liquid extraction includes using diatomaceous earth and an organic water-immiscible solvent system, and wherein the organic water-immiscible solvent system comprises a solvent selected from the group consisting of hexane, octanol, chloroform, dichloromethane, diethyl ether, cyclohexane, pentane, N-heptanes, benzene, n-butyl chloride, butanol, methylene chloride, and mixtures thereof;
 (c) chromatographically separating testosterone from the other components in the partially purified sample using reverse phase liquid chromatography, wherein the liquid chromatography comprises using at least one guard column; and
 (d) analyzing the chromatographically separated testosterone by mass spectrometry to determine the amount of testosterone in the biological sample;
 wherein the step of partially purifying the biological sample using supported liquid extraction comprises eluting with the organic water-immiscible solvent system under slight vacuum and under gravity.

22. A method of generating a report useful for diagnosing a disease or condition associated with abnormal testosterone levels, the method comprising:
 (a) providing a biological sample comprising testosterone;
 (b) partially purifying the biological sample using supported liquid extraction to provide a partially purified sample comprising testosterone, wherein the supported liquid extraction includes using diatomaceous earth and an organic water-immiscible solvent system, and wherein the organic water-immiscible solvent system comprises a solvent selected from the group consisting of hexane, octanol, chloroform, dichloromethane, diethyl ether, cyclohexane, pentane, N-heptanes, benzene, n-butyl chloride, butanol, methylene chloride, and mixtures thereof;
 (c) chromatographically separating testosterone from the other components in the partially purified sample using liquid chromatography, wherein the liquid chromatography comprises using at least one guard column;
 (d) analyzing the chromatographically separated testosterone by mass spectrometry to determine the amount of testosterone in the biological sample; and
 (e) generating a report that recites the concentration of testosterone in the biological sample;
 wherein the step of partially purifying the biological sample using supported liquid extraction comprises eluting with the organic water-immiscible solvent system under slight vacuum and under gravity.

23. A system for determining the presence or amount of testosterone in a biological sample, the system comprising:
 (a) a station for partially purifying a biological sample using supported liquid extraction to provide a partially purified sample, wherein the supported liquid extraction includes using diatomaceous earth and eluting with an organic water-immiscible solvent system under slight vacuum and under gravity, and wherein the organic water-immiscible solvent system comprises a solvent selected from the group consisting of hexane, octanol, chloroform, dichloromethane, diethyl ether, cyclohexane, pentane, N-heptanes, benzene, n-butyl chloride, butanol, methylene chloride, and mixtures thereof;
 (b) a station for chromatographically separating testosterone from the other components in the partially purified sample using liquid chromatography, wherein the liquid chromatography comprises using at least one guard column; and
 (c) a station for analyzing the chromatographically separated testosterone by mass spectrometry to determine the presence or amount of testosterone in the biological sample.

* * * * *